(12) United States Patent
Koski

(10) Patent No.: US 6,441,143 B1
(45) Date of Patent: *Aug. 27, 2002

(54) METHODS AND COMPOSITIONS FOR DETERMINING HER-2/NEU EXPRESSION

(75) Inventor: Raymond A. Koski, Old Lyme, CT (US)

(73) Assignee: Amgen INC, Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/046,783

(22) Filed: Mar. 23, 1998

Related U.S. Application Data

(63) Continuation of application No. 08/421,356, filed on Apr. 13, 1995, now Pat. No. 5,783,404.

(51) Int. Cl.[7] .................. C07K 16/00; C12P 21/08; G01N 33/53; G01N 33/567; G01N 33/574

(52) U.S. Cl. .................. 530/388.85; 530/387.1; 530/387.7; 530/388.1; 435/7.1; 435/7.2; 435/7.21; 435/7.23

(58) Field of Search .................. 424/141.1, 142.1, 424/155.1, 130.1, 138.1; 530/387.1, 387.7, 388.85, 388.1; 435/7.1, 7.2, 7.21, 7.23

(56) References Cited

U.S. PATENT DOCUMENTS

| | | | |
|---|---|---|---|
| 4,465,776 A | * | 8/1984 | Cidlowski et al. |
| 4,968,603 A | | 11/1990 | Slamon et al. |
| 5,066,581 A | | 11/1991 | Suciu-Foca et al. |
| 5,783,404 A | * | 7/1998 | Koski |

FOREIGN PATENT DOCUMENTS

| | | |
|---|---|---|
| EP | 0 225 579 A2 | 6/1987 |
| WO | WO89/06692 | 7/1989 |
| WO | WO89/10412 | 11/1989 |
| WO | WO93/03741 | 3/1993 |

OTHER PUBLICATIONS

Berchuck et al. Cancer Res 50, 4087–4091 (1990).
Burnette et al. Bio/Technology 6, 699–706 (1988).
Carter et al. Cancer 63, 181–187 (1989).
Caruthers, Science 230, 281 (1985).
Clark et al. Cancer Res. 51, 944–948 (1991).
Corbett et al. J. Path. 161, 15–25 (1990).
Coussens et al. Science 230, 1132–1139 (1985).
Fendly et al. Cancer Res. 50, 1550–1558 (1990).
Gullick et al. Int. J. Cancer 40, 246–254 (1987).
Harlow and Lane *Antibodies: A Laboratory Manual,* Cold Spring Harbor Laboratory (1988).
Hopp et al. PNAS, USA 78, 3824–3828 (1981).
Kallioniemi et al. Int. J. Cancer 49, 650–655 (1991).
King et al. Science 229, 974–976 (1985).
Kury et al. Eur. J. Cancer 26, 946–949 (1990).
Landreth et al., Blood 80, 1207–1212 (1992).
Landreth et al., Journal of Immunology 140, 845–852 (1988).

(List continued on next page.)

*Primary Examiner*—Anthony C. Caputa
*Assistant Examiner*—Jennifer Hunt
(74) *Attorney, Agent, or Firm*—Finnegan, Henderson, Farabow, Garrett & Dunner, L.L.P.

(57) ABSTRACT

Anti-p185$^{HER-2/neu}$ antibodies which are useful in the detection of HER-2/neu oncogene overexpression in biological samples are described. The antibodies are accurate and reliable in immunocytochemical or immunohistochemical assays of cell and tissue samples. Also described are methods for detecting HER-2/neu oncogene expression in a biological sample using the antibodies of the invention and a diagnostic kit comprising the antibodies. The reagents provide an accurate means of identifying certain cancer patients who have the greatest probability of relapse and/or the least likelihood of survival.

19 Claims, 6 Drawing Sheets

OTHER PUBLICATIONS

Maniatis et al., *Molecular Cloning: A Laboratory Manual,* Cold Spring Harbor Laboratory (1982).
Muss et al. N. Engl. J. Med. 330, 1260–1266 (1994).
Namen et al., Journal Exp. Med. 167, 988–1002 (1988).
Osborne, in *Breast Diseases,* Harris, J.R. et al., eds. 2nd ed. J.B. Lippincott, pp. 301–325 (1991).
Press, Cancer Res. 54, 2771–2777 (1994).
Rilke et al. Int. J. Cancer 49, 44–49 (1991).
Ro et al. Cancer Res. 49, 6941–6944 (1989).
Rubin et al. Am. J. Obstet. Gynecol. 168, 162–169 (1993).
Schecter et al Science 229, 976–978 (1985).
Scott et al., J. Biol. Chem. 266, 14300–14305 (1991).
Semba et al. PNAS, USA 82, 6497–6501 (1985).
Slamon et al. Cancer Cells 7, 371–384 (1989).
Slamon et al. Science 235, 177–182 (1987).
Slamon et al. Science 244, 707–712 (1989).
Van de Vijver et al. Cancer Cells 7, 385–391 (1989).
Van de Vijver et al. N. Engl. J. Med. 319, 1239–1245 (1988).
Walker et al. Brit. J. Cancer 60, 426–429 (1989).
Woodward et al., Biological Abstracts 90(4), abstract No. 35798 (1990).
Wright et al. Cancer Res. 49, 2087–2090 (1989).
Zhou et al. Oncogene 4, 105–108 (1989).
Zola, *Monoclonal Antibodies: A Manual of Techniques,* CRC Press, Boca Raton, FL (1987).

* cited by examiner

FIG. 1A

```
            10            20            30            40            50            60
       150-1                                      150-3
   TCTAGAAGGAGGAATAACATATGCTCCAGCGTCTGCGTATTGTACGTGGTACCCAGCTCT
   AGATCTTCCTCCTTATTGTATACGAGGTCGCAGACGCATAACATGCACCATGGGTCGAGA
              150-2                              150-4

70            80            90           100           110           120
       150-5                                      150-7
   TCGAAGATAACTACGCACTGGCTGTACTGGACAACGGTGATCCTCTGAACAACACCACTC
   AGCTTCTATTGATGCGTGACCGACATGACCTGTTGCCACTAGGAGACTTGTTGTGGTGAG
              150-6                              150-8

130           140           150           160           170           180
       150-9                                     150-11
   CGGTAACTGGTGCTTCTCCTGGCGGTCTGCGTGAACTGCAGCTCCGTAGCTTGACTGAAA
   GCCATTGACCACGAAGAGGACCGCCAGACGCACTTGACGTCGAGGCATCGAACTGACTTT
             150-10                             150-12

190           200           210           220           230           240
      150-13         150-15                      150-17
   TCCTCAAAGGTGGCGTACTGATCCAGCGTAACCCTCAGCTGTGCTATCAGGATACTATCC
   AGGAGTTTCCACCGCATGACTAGGTCGCATTGGGAGTCGACACGATAGTCCTATGATAGG
            150-14         150-16                     150-18

250           260           270           280           290           300
      150-19                       150-21                  150-23
   TGTGGAAAGACATCTTCCACAAGAACAACCAGCTGGCTCTGACTCTGATCGACACCAACC
   ACACCTTTCTGTAGAAGGTGTTCTTGTTGGTCGACCGAGACTGAGACTAGCTGTGGTTGG
             150-20                     150-22          150-24

310           320
   GTTCTCGAGCTTAATAGGATCC
   CAAGAGCTCGAATTATCCTAGG
```

FIG.1B

Met Leu Gln Arg Leu Arg Ile Val Arg Gly Thr Gln Leu Phe

Glu Asp Asn Tyr Ala Leu Ala Val Leu Asp Asn Gly Asp Pro

Leu Asn Asn Thr Thr Pro Val Thr Gly Ala Ser Pro Gly Gly

Leu Arg Glu Leu Gln Leu Arg Ser Leu Thr Glu Ile Leu Lys

Gly Gly Val Leu Ile Gln Arg Asn Pro Gln Leu Cys Tyr Gln

Asp Thr Ile Leu Trp Lys Asp Ile Phe His Lys Asn Asn Gln

Leu Ala Leu Thr Leu Ile Asp Thr Asn Arg Ser Arg Ala

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
       (A) LENGTH: 322 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 1:

TCTAGAAGGA GGAATAACAT ATGCTCCAGC GTCTGCGTAT TGTACGTGGT ACCCAGCTCT      60

TCGAAGATAA CTACGCACTG GCTGTACTGG ACAACGGTGA TCCTCTGAAC AACACCACTC     120

CGGTAACTGG TGCTTCTCCT GGCGGTCTGC GTGAACTGCA GCTCCGTAGC TTGACTGAAA     180

TCCTCAAAGG TGGCGTACTG ATCCAGCGTA ACCCTCAGCT GTGCTATCAG GATACTATCC     240

TGTGGAAAGA CATCTTCCAC AAGAACAACC AGCTGGCTCT GACTCTGATC GACACCAACC     300

GTTCTCGAGC TTAATAGGAT CC                                             322

(2) INFORMATION FOR SEQ ID NO: 2:

(i) SEQUENCE CHARACTERISTICS:
       (A) LENGTH: 322 base pairs
       (B) TYPE: nucleic acid
       (C) STRANDEDNESS: double
       (D) TOPOLOGY: linear (ii) MOLECULE TYPE: cDNA (xi) SEQUENCE DESCRIPTION: SEQ ID NO: 2:

AGATCTTCCT CCTTATTGTA TACGAGGTCG CAGACGCATA ACATGCACCA TGGGTCGAGA      60

AGCTTCTATT GATGCGTGAC CGACATGACC TGTTGCCACT AGGAGACTTG TTGTGGTGAG     120

GCCATTGACC ACGAAGAGGA CCGCCAGACG CACTTGACGT CGAGGCATCG AACTGACTTT     180

AGGAGTTTCC ACCGCATGAC TAGGTCGCAT TGGGAGTCGA CACGATAGTC CTATGATAGG     240

ACACCTTTCT GTAGAAGGTG TTCTTGTTGG TCGACCGAGA CTGAGACTAG CTGTGGTTGG     300

CAAGAGCTCG AATTATCCTA GG                                             322

(2) INFORMATION FOR SEQ ID NO: 3:

(i) SEQUENCE CHARACTERISTICS:
       (A) LENGTH: 97 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO: 3:

Met Leu Gln Arg Leu Arg Ile Val Arg Gly Thr Gln Leu Phe Glu Asp
1               5                   10                  15

Asn Tyr Ala Leu Ala Val Leu Asp Asn Gly Asp Pro Leu Asn Asn Thr
                20                  25                  30

Thr Pro Val Thr Gly Ala Ser Pro Gly Gly Leu Arg Glu Leu Gln Leu
            35                  40                  45

```
Arg Ser Leu Thr Glu Ile Leu Lys Gly Gly Val Leu Ile Gln Arg Asn
    50                  55                  60

Pro Gln Leu Cys Tyr Gln Asp Thr Ile Leu Trp Lys Asp Ile Phe His
65                  70                  75                  80

Lys Asn Asn Gln Leu Ala Leu Thr Leu Ile Asp Thr Asn Arg Ser Arg
                85                  90                  95

Ala
```

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CTAGAAGGAG GAATAACATA TGCTCC                                        26
```

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
CGCTGGAGCA TATGTTATTC CTCCTT                                        26
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
AGCGTCTGCG TATTGTACGT GGTA                                          24
```

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
TGGGTACCAC GTACAATACG CAGA                                          24
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

CCCAGCTCTT CGAAGATAAC TACGCACTGG CTGT                                                34

(2) INFORMATION FOR SEQ ID NO: 9:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 9:

CAGTACAGCC AGTGCGTAGT TATCTTCGAA GAGC                                                34

(2) INFORMATION FOR SEQ ID NO: 10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 10:

ACTGGACAAC GGTGATCCTC TGAACAA                                                         27

(2) INFORMATION FOR SEQ ID NO: 11:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 11:

GGTGTTGTTC AGAGGATCAC CGTTGTC                                                         27

(2) INFORMATION FOR SEQ ID NO: 12:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 12:

CACCACTCCG GTAACTGGTG CTTCTCC                                                         27

(2) INFORMATION FOR SEQ ID NO: 13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 13:

GCCAGGAGAA GCACCAGTTA CCGGAGT                                              27

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TGGCGGTCTG CGTGAACTGC AGCTCCGT                                             28

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 15:

AGCTACGGAG CTGCAGTTCA CGCAGACC                                             28

(2) INFORMATION FOR SEQ ID NO: 16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 16:

AGCTTGACTG AAATCCTCAA AGGTG                                                25

(2) INFORMATION FOR SEQ ID NO: 17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 17:

ACGCCACCTT TGAGGATTTC AGTCA                                                25

(2) INFORMATION FOR SEQ ID NO: 18:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GCGTACTGAT CCAGCGTAAC CCTCA                                                25

(2) INFORMATION FOR SEQ ID NO: 19:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

CAGCTGAGGG TTACGCTGGA TCAGT                                          25

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 20:

GCTGTGCTAT CAGGATACTA TCCT                                           24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 21:

CCACAGGATA GTATCCTGAT AGCA                                           24

(2) INFORMATION FOR SEQ ID NO: 22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 22:

GTGGAAAGAC ATCTTCCACA AGA                                            23

(2) INFORMATION FOR SEQ ID NO: 23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 23:

TTGTTCTTGT GGAAGATGTC TTT                                            23

(2) INFORMATION FOR SEQ ID NO: 24:

(i) SEQUENCE CHARACTERISTICS:
        (A) LENGTH: 19 base pairs

-continued

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 24:

ACAACCAGCT GGCTCTGAC                                                 19

(2) INFORMATION FOR SEQ ID NO: 25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 25:

CAGAGTCAGA GCCAGCTGG                                                 19

(2) INFORMATION FOR SEQ ID NO: 26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 26:

TCTGATCGAC ACCAACCGTT CTCGAGCTTA ATAG                                34

(2) INFORMATION FOR SEQ ID NO: 27:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 27:

GATCCTATTA AGCTCGAGAA CGGTTGGTGT CGAT                                34
```

METHODS AND COMPOSITIONS FOR DETERMINING HER-2/NEU EXPRESSION

This application is a continuation of U.S. Ser. No. 08/421,356, now U.S. Pat. No. 5,783,404.

The invention relates to certain anti-p185$^{HER-2/neu}$ antibodies and the use of said antibodies in assays for the determination of HER-2/neu expression levels in biological samples. The antibodies of the invention are accurate indicators of HER-2/neu overexpression in human cancerous tissue using immunocytochemical or immunohistochemical assays. These reagents are useful for identifying cancer patients who have the greatest probability of relapse and/or the least likelihood of survival and, as a result, may be likely to benefit from adjuvant therapy.

BACKGROUND OF THE INVENTION

Prognostic factors often help predict relapse and survival in patients suffering from cancer. The presence of certain factors that are indicative of a greater probability of relapse and/or a low probability of survival may suggest that adjuvant therapy is appropriate. High-dose chemotherapy or autologous bone marrow transplantation are possible treatment regimens after surgery. The existence of reliable prognostic factors to predict relapse and survival are important since aggressive cancer therapy is costly and is frequently accompanied by toxic side effects. Likewise, the absence of such factors may indicate that less intensive therapy is required. Prognostic factors that have been used to predict relapse in breast cancer patients include tumor size (Carter et al. Cancer 63, 181–187 (1989)), number of lymph nodes involved (Carter et al., supra), histologic grade (Henson et al. Cancer 68, 2142–2149 (1991)), and the presence of estrogen or progesterone receptors (Osborne, in *Breast Diseases*, Harris, J. R. et al., eds. 2nd ed. J. B. Lippincott, pp. 301–325 (1991)). Recently, a variety of molecular markers have shown potential as prognostic factors for identifying cancer patients, particularly those suffering from breast and ovarian cancer, that are most likely to benefit from aggressive cancer therapy. Molecular markers that may be important include measurements of DNA content, cell proliferation and oncogene expression. Oncogene expression has received some attention by investigators in view of the apparent correlation between expression of the HER-2/neu oncogene and poor prognosis in patients with breast cancer. However, as explained below, this correlation has not been observed by all investigators or has been observed in only a subset of patients examined.

The HER-2/neu oncogene encodes a membrane-associated glycoprotein referred to as p185$^{HER-2/neu}$ having extracellular, transmembrane and intracellular domains, with the extracellular domain having homology to that of the epidermal growth factor receptor. The human gene, designated as c-erbB-2, HER-2, or neu, was reported by Semba et al. (Proc. Natl. Acad. Sci. USA 82, 6497–6501 (1985)); Coussens et al. (Science 230, 1132–1139 (1985)) and King et al. (Science 229, 974–976 (1985)). A related rat gene was reported by Schecter et al (Science 229, 976–978 (1985)).

Increased expression of the HER-2/neu oncogene in tumor cells and cell lines has been reported by several groups (Coussens et al., supra; King et al., supra). The increased expression of HER-2/neu results from gene amplification or increased expression of the single copy gene. These observations suggested that HER-2/neu may be overexpressed in human cancer tissue. Slamon and colleagues (Slamon et al. Science 235, 177–182 (1987); Slamon et al. Science 244, 707–712 (1989)) examined HER-2/neu expression levels in tumors taken from a large sample of breast and ovarian cancer patients. It was found that nearly 30% of those patients had amplification of the HER-2/neu gene, that the amplification was associated with overexpression, and that overexpression of HER-2/neu was associated with a poor clinical outcome (increased relapse and low survival rate) particularly in node-positive breast cancer patients. The correlations reported by Slamon have been confirmed in a number of studies (see, for example, Ro et al. Cancer Res. 49, 6941–6944 (1989); Walker et al. Brit. J. Cancer 60, 426–429 (1989); Wright et al. Cancer Res. 49, 2087–2090 (1989); Berchuck et al. Cancer Res 50, 4087–4091 (1990); Kallioniemi et al. Int. J. Cancer 49, 650–655 (1991); Rilke et al. Int. J. Cancer 49, 44–49 (1991)). However, other investigators have not found a significant correlation between prognosis and HER-2/neu overexpression in breast and ovarian cancer (see, for example, Van de Vijver et al. N. Engl. J. Med. 319, 1239–1245 (1988); Zhou et al. Oncogene 4, 105–108 (1989); Clark et al. Cancer Res. 51, 944–948 (1991); Kury et al. Eur. J. Cancer 26, 946–949 (1990); Rubin et al. Am. J. Obstet. Gynecol. 168, 162–169 (1993)). Presently, it is not clear in the art as to the reliability of HER-2/neu overexpression as a prognostic factor in breast and other cancers.

Most studies reported to date that have examined HER-2/neu expression levels in human breast cancer tissue specimens have employed immunohistochemical analysis of fixed paraffin-embedded tissue samples. A variety of anti-p185$^{HER-2/neu}$ antibodies have been generated and used in evaluating HER-2/neu expression (see, for example, van de Vijver et al. Cancer Cells 7, 385–391 (1989); Gullick et al. Int. J. Cancer 40, 246–254 (1987); Corbett et al. J. Path. 161, 15–25 (1990); Fendly et al. Cancer Res. 50, 1550–1558 (1990); Slamon et al. Cancer Cells 7, 371–380 (1989)). In view of the contradictory conclusions regarding the predictive value of HER-2/neu expression levels in breast cancer tissue, Press et al. (Cancer Res. 54, 2771–2777 (1994)) undertook a systematic evaluation of 28 different anti-p185$^{HER-2/neu}$ antibodies using multi-tumor tissue blocks. They observed significant variability in the detection of HER-2/neu expression levels in the same tissue samples by different antibodies. It has become apparent that the antibody used in the analysis of HER-2/neu expression is a crucial reagent that can significantly affect the reliability of HER-2/neu expression as a prognostic tool.

U.S. Pat. No. 4,968,603 discloses methods for screening patients suffering from breast and ovarian cancer for HER-2/neu expression or amplification. Expression of the HER-2/neu gene can be measured in one instance by immunohistochemical staining using an antibody raised against part or all of the HER-2/neu polypeptide. This disclosure does not provide anti-p185$^{HER-2/neu}$ antibodies nor does it suggest the variability with which different anti-p185$^{HER-2/neu}$ antibodies may react with p185$^{HER-2/neu}$ protein in biological samples. PCT Application No. WO89/10412 discloses antibodies to HER-2/neu protein generated by using NIH 3T3 cells transfected with a HER-2/neu full-length cDNA clone as the immunogen. Also disclosed are methods for detecting HER-2/neu overexpression using anti-p185$^{HER-2/neu}$ antibodies. PCT Application No. WO89/06692 discloses antibodies raised to NIH 3T3 cells transfected with full-length HER-2/neu cDNA clone and discloses methods for detecting tumors expressing HER-2/neu using anti-p185$^{HER-2/neu}$ antibodies. PCT Application No. WO93/03741 discloses antibodies raised to SK-BR-3 human breast cancer cells as an immunogen. None of these applications describe the reaction of anti-p185$^{HER-2/neu}$ antibodies with human cancer tissue samples. In addition, none of these applications address the problem of variable reactivity of anti-p185$^{HER-2/neu}$ antibodies with HER-2/neu protein in tissue samples.

It has been recently reported (Muss et al. N. Engl. J. Med. 330, 1260–1266 (1994)) that node-positive breast cancer patients treated with high-dose chemotherapy had significantly longer time to relapse and longer survival time if their tumors had HER-2/neu overexpression, while patients with little or no HER-2/neu expression showed no significant benefit to increased dosage.

In view of the potential importance of HER-2/neu overexpression in predicting response to treatment in certain cancers, it is desirable to identify reagents which will accurately and reliably measure levels of HER-2/neu expression. In particular, it is desirable to develop anti-p185$^{HER-2/neu}$ antibodies which are useful for detection of HER-2/neu expression in cell and tissue specimens using immunostaining techniques. It is desirable that the antibodies react strongly with biological samples that exhibit HER-2/neu overexpression while, at the same time, react poorly or not at all with samples expressing HER-2/neu at normal levels.

SUMMARY OF THE INVENTION

The invention relates to anti-p185$^{HER-2/neu}$ monoclonal antibodies or antibody fragments thereof which bind to denatured epitopes comprising a subset of amino acids residues 96–191 of the HER-2/neu protein as shown in FIG. 1B (SEQ ID NO: 3). The antibodies recognize HER-2/neu protein in biological samples that have been treated with a fixative, but recognize poorly, or not at all, HER-2/neu protein in its native conformation in biological samples.

Anti-p185$^{HER-2/neu}$ antibodies of the invention will react strongly with biological sample having HER-2/neu overexpression, but will react weakly or not at all with samples having normal levels of HER-2/neu expression. Preferably, the antibodies will react strongly with at least 80% of cancer specimens (tissues or cells) which overexpress HER-2/neu and will react weakly or not at all with cancer specimens which express HER-2/neu at normal levels. In one embodiment, the antibody is selected from the group consisting of antibodies 9C2 and 11G5. Also encompassed by the invention are hybridoma cell lines producing such antibodies.

The invention also relates to a method for detecting HER-2/neu expression in a biological sample by contacting the sample with an anti-p185$^{HER-2/neu}$ antibody of the present invention under conditions appropriate for antibody binding to the sample, and determining the extent of antibody binding to the sample. Preferably, the biological sample is a cell or tissue specimen derived from stomach, lung, breast, pancreatic, prostate or ovarian cancer which is treated with a fixative prior to analysis.

The invention also relates to a kit for use in detecting HER-2/neu expression in a biological sample using the antibodies of the present invention.

DESCRIPTION OF THE FIGURES

FIG. 1. (a) Sequence of a synthetic gene encoding the HER-2/neu (96–191) extracellular domain protein fragment produced by assembly of oligonucleotides 150-1 to 150-24. (b) Amino acid sequence of HER-2/neu (96–191) polypeptide fragment.

DETAILED DESCRIPTION OF THE INVENTION

Figure 2A:
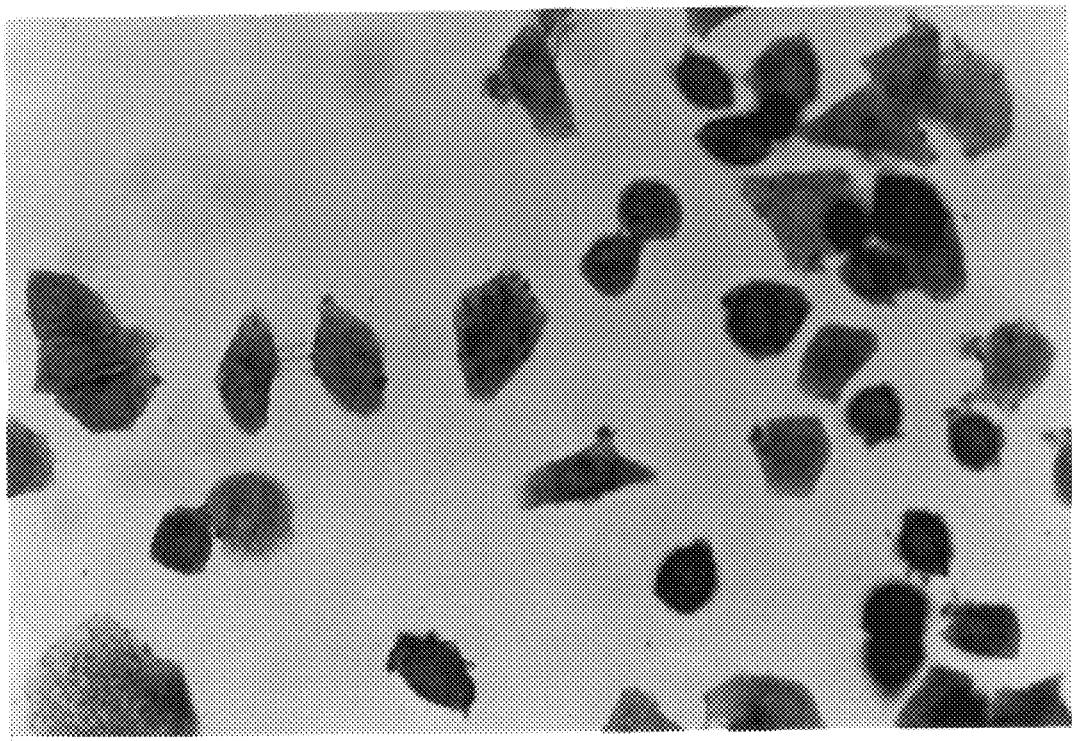
FIG. 2. Immunocytochemical staining of cell lines. Cultured cell lines were fixed with Saccamanno fluid and immunoperoxidase stained with 9C2 antibody. Staining of SK-BR-3 human breast adenocarcinoma cells is shown in panel a. Panels b shows staining of CHO-HER-2 B7 cells, which are Chinese hamster ovary (CHO) cells transfected with a vector that directs expression of elevated levels of human p185$^{HER-2/neu}$. Staining of CHO-PCN cells, which are transfected with a negative control vector, is shown in panel c. All prints represent identical exposure times.

As used herein, the term "HER-2/neu" refers to HER-2/neu nucleic acid sequences, and the terms "p185$^{HER-2/neu}$" and "HER-2/neu protein" refer to the encoded protein.

The invention provides for anti-p185$^{HER-2/neu}$ antibodies which are useful for quantifying levels of HER-2/neu expression in biological samples. More particularly, the antibodies are useful in immunocytochemical and immunohistochemical analysis of cancer tissue for HER-2/neu expression levels. Overexpression of HER-2/neu may represent a prognostic factor indicating time to relapse and probability of survival for breast and ovarian cancer patients. Aggressive treatment regimens after surgery may be indicated for those patients whose tumors exhibit elevated levels of HER-2/neu protein.

The antibodies of the present invention were raised against a HER-2/neu extracellular domain protein fragment prepared as described in Example 1. This fragment, encompassing amino acid residues 96–191 of the HER-2/neu polypeptide, was chosen for its likely antigenicity and relatively low homology to human epidermal growth factor (EGF) receptor. Monoclonal antibodies to the HER-2/neu extracellular domain protein fragment were generated using standard techniques and high titer hybridomas were subjected to dilution cloning and further screened in ELISAs for reaction with the HER-2/neu 96–191 fragment (see Example 2). Dilution clones which were strongly positive were further characterized for binding to the HER-2/neu protein expressed in transfected CHO cells (Example 3A) and in breast tumor samples (Example 3B).

The antibodies of the present invention encompass monoclonal antibodies and fragments thereof which bind to denatured epitopes comprising a subset of amino acids residues 96–191 of the HER-2/neu protein as shown in FIG. 1B (SEQ ID NO:3). The antibodies recognize HER-2/neu protein in biological samples that have been treated with a fixative which denatures protein antigens (see Example 3) but react poorly, or not at all, with HER-2/neu protein in biological samples which have not been treated with a fixative. Samples having HER-2/neu protein in a denatured conformation include cells and tissues that have been fixed for immunocytochemistry or immunohistochemistry. On the other hand, cells expressing HER-2/neu which have not been treated with a fixative (e.g., actively proliferating cells or cells prepared for flow cytometry) will have HER-2/neu protein in a native conformation. As used herein, the term "epitope" refers to the region of the HER-2/neu polypeptide bound by an anti-p185$^{HER-2/neu}$ antibody, wherein the binding prevents association of a second anti-p185$^{HER-2/neu}$ antibody. In the present invention, the epitope recognized by a p185$^{HER-2/neu}$ antibody comprises a subset of amino acids 96–191 of the HER-2/neu protein. The term "native" refers to the presence of a naturally occurring three-dimensional protein conformation whereas the term "denatured" refers to either the absence of part or all of the naturally-occurring conformation or to the presence of a non-naturally occurring three-dimensional conformation.

Antibody fragments include those portions of the antibody which bind to the epitope on the HER-2/neu protein described above. Examples of such fragments include Fab and F(ab') fragments generated by enzymatic cleavage of full-length antibodies. Other binding fragments include those generated by recombinant DNA techniques, such as expression of recombinant plasmids containing nucleic acid sequences encoding antibody variable regions.

Anti-p185$^{HER-2/neu}$ antibodies have been used previously to detect HER-2/neu expression levels in cell and tissue samples. However, the antibodies described herein have distinct advantages over the antibodies in the art in that they have enhanced sensitivity and specificity in detecting HER-2/neu overexpression in human cancer specimens (cells or tissues) that have been treated with a fixative. The term "sensitivity" refers to the ability of an (antibody to react strongly with cells or tissues which exhibit HER-2/neu overexpression) The term "specificity" refers to the ability of an antibody to react weakly or inability to react at all with cells or tissues which exhibit normal HER-2/neu expression. It is anticipated that cells or tissues having greater than about two-fold overexpression of HER-2/neu will be detected by the antibody, and preferably greater than about five-fold overexpression will be detected. The optimal antibodies for detecting HER-2/neu overexpression will have a high sensitivity (few false negatives) and high specificity (few false positives). Anti-p185$^{HER-2/neu}$ antibodies having these properties will be more reliable reagents for predicting whether a given sample has elevated levels of HER-2/neu protein and, in turn, for predicting rate of relapse and length of survival after surgery.

Press and colleagues (Press et al. supra) have tested 28 different anti-p185$^{HER-2/neu}$ antibodies for immunostaining of fixated and paraffin-embedded breast cancer tissues having known levels of HER-2/neu amplification and/or overexpression. Many of the antibodies tested had 100% specificity, i.e., no false positives, yet the sensitivities for HER-2/neu staining ranged from 2% to greater than 80%. Unexpectedly, it was observed (see Table 2 on p. 2774) that antibodies 9C2 and 11G5 disclosed herein had 80% or greater sensitivity for immunostaining breast cancers and had the highest combined sensitivity and specificity of immunostaining for any of the monoclonal antibodies tested. Further, 9C2 had among the highest combined sensitivity (greater than 80%) and specificity (100%) of immunostaining of any of the antibodies tested whether polyclonal or monoclonal. The antibodies of the present invention retain the specificity for HER-2/neu protein immunostaining characteristic of other anti-p185$^{HER-2/neu}$ antibodies while at the same time show markedly increased sensitivity, and therefore represent a significant improvement over the antibodies previously available. Preferably, antibodies of the invention will detect HER-2/neu overexpression in 80% or more of those tissues known to have elevated levels of HER-2/neu protein. In another embodiment, it is preferred that the antibodies have 100% specificity, that is the antibodies do not yield false positive results on immunostaining of biological samples.

The anti-p185$^{HER-2/neu}$ antibodies in the prior art have either been raised against the entire extracellular domain of HER-2/neu expressed on viable cell surfaces or against HER-2/neu peptides which are distinct from the region of amino acids 96–191 used herein. (See "Background" section for citation of references to anti-p185$^{HER-2/neu}$ antibodies). The properties of the anti-p185$^{HER-2/neu}$ antibodies of the present invention suggest that they recognize a denatured epitope of the HER-2/neu (96–191) extracellular domain. This may explain the improved sensitivity of the antibodies that was observed in the studies reported by Press et al. supra.

Also encompassed by the invention are the hybridoma cell lines which produce the antibodies of the invention. In one embodiment, the hybridoma cell lines produce antibodies designated 9C2 and 11G5. A dilution clone of the hybridoma cell line which produces the 9C2 antibody (designated 9C2C1A9) was deposited with the American Type Culture Collection, Rockville, Md. on Mar. 14, 1995 with accession no. HB 11862. A dilution clone of the hybridoma cell line which produces the 11G5 antibody (designated 11G5G1B11) was deposited with the American Type Culture Collection, Rockville, Md. on Mar. 14, 1995 under accession no. HB 11861.

Also encompassed by the invention is a method for detecting HER-2/neu expression in a biological sample by contacting the sample with an anti-p185$^{HER-2/neu}$ antibody of the present invention under conditions appropriate for antibody binding to the sample, and determining the extent of antibody binding to the sample wherein the improvement comprises contacting the sample of the anti-p185$^{HER-2/neu}$ antibodies of the invention. The biological sample may be a fluid (blood, serum, urine, semen), intact cells or extracts thereof, or tissue samples. Preferably., the sample is a clinical cytology specimen (e.g, fine needle breast biopsy and pulmonary cytology specimen) or a human tissue specimen from, for example, stomach, lung, breast, ovarian, pancreatic or prostate tumors. The method of detecting HER-2/neu expression may employ any suitable immunoassay, such as a solution assay (radioimmunoassay, enzyme-linked immunosorbent assay), immunoblotting, or cell or tissue imunostaining. In a preferred embodiment, the method of detection is cell or tissue immunostaining. Biological samples may be processed prior to contacting antibody by a variety of methods available to one skilled in the art. In one embodiment, the sample (usually a cell or tissue specimen) has been treated with a fixative suitable for subsequent immunocytochemical or immunohistochemical analysis. The appropriate fixatives are known in the art and include organic solvents (alcohols and acetone) or cross-linking reagents (formaldehyde or glutaraldehyde).

It is anticipated that the antibodies of the invention will be useful in assays where the antigen to be identified exists among many other cell or tissue components. In these instances, the extent of antibody binding may be detected by a label attached directly to the antibody such as a radioactive ($I^{125}$), chemical (biotin), fluorescent (fluorescein or rhodamine) or enzymatic (horseradish peroxidase or alkaline phosphatase) label. Alternatively, a double antibody assay may be used wherein the primary antibody is an anti-p185$^{HER-2/neu}$ antibody which, when bound to antigen, is detected by a second antibody which will bind specifically to the primary antibody (e.g., anti-mouse IgG antibody). The second antibody will have a detectable label selected from those described above.

The invention also relates to a kit for use in detecting HER-2/neu expression in a biological sample comprising the antibodies of the present invention. Preferably, the antibodies are 9C2 and 11G5. In addition to antibody, the kit may include any additional reagents necessary for determining HER-2/neu expression levels in a biological sample. Such reagents may include a secondary antibody, a detectable label, blocking serum, positive and negative control samples and detection reagents.

Procedures for immunizing animals, generating and culturing hybridomas, screening for antibody production and performing various immunoassays are described herein or were carried out essentially as described in Harlow and Lane *Antibodies: A Laboratory Manual*, Cold Spring Harbor Laboratory (1988) and Zola, *Monoclonal Antibodies: A Manual of Techniques*, CRC Press, Boca Raton, Fla. (1987), the relevant portions of which are incorporated herein by reference. Recombinant DNA techniques are described herein or were carried out essentially as described in Maniatis et al., *Molecular, Cloning: A Laboratory Manual*, Cold Spring Harbor Laboratory (1982) the relevant portions of which are incorporated herein by reference.

The following examples are offered to more fully illustrate the invention, but are not construed as limiting the scope thereof.

EXAMPLE 1

Construction and Expression of a HER-2/neu Extracellular Domain Peptide Fragment The human c-erbB-2 or HER-2/neu gene has been cloned and sequenced by several groups (Semba et al. supra; Coussens et al. supra; King et al. supra). The extracellular domain of HER-2/neu corresponds to amino acids residues 1–650 where residue 1 is the amino terminal methionine and residue 651 corresponds to the start of the transmembrane domain. This region was examined by sequence composition, hydrophilicity and structural parameters to define a region of about 100 amino acid residues that would be suitable as a HER-2/neu immunogen.

Amino acid residues 1–650 of HER-2/neu are characterized by four distinct domains. Domain I spanning residues 1–190 represents the amino terminal portion of the protein and possesses four possible N-glycosylation sites and four cysteine residues. Domain II extends from residues 191 through residue 343 and contains 23 cysteine residues. This cysteine rich region was deemed unsuitable for a synthetic gene due to possible protein aggregation and/or refolding problems. Domain III (amino acid residues 344–502) along with Domain I has relatively few cysteines. Domain IV (amino acid residues 503–649) is another cysteine rich domain (21 cysteine residues) and was again considered unsuitable for initial synthetic gene expression work.

Domain I (a.a. 1–190) was examined in further detail to locate the best subregion with antigenic character. Hopp and Woods analysis (Hopp et al. Proc. Natl. Acad. Sci. USA 78, 3824–3828 (1981)) shows that amino acids 1–95 contains only 24% net hydrophilic character while region 96–191 contains 43% net hydrophilic residues. Hydrophilicity is a good indication of protein regions that are likely to be located on the surface of the folded structure. Their surface accessibility makes them potential antigenic epitopes.

The HER-2/neu protein has strong homology to the epidermal growth factor (EGF) receptor. Therefore, Domains I–IV were evaluated for sequence homology to the EGF-receptor protein. The relative homology for each domain was I:42%, II:49%, III:40%, and IV:44%. The homology of two subregions of Domain I to EGF receptor were found to be 1–95:46% and 96–191:37%. The lower homology of the region 96–191 (37%) was considered advantageous in ensuring that the antibody generated to HER-2/neu does not also recognize the EGF receptor protein.

As a result of this examination, a synthetic gene was designed to encode the HER-2/neu protein fragment having amino acids residues 96–191. The resulting protein fragment is useful for raising anti-HER2 antibodies.

The synthetic gene was divided into 24 oligonucleotides for DNA synthesis as shown in Table 1:

TABLE 1

```
SEQ ID NO. 4:
5' CTA GAA GGA GGA ATA ACA TAT GCT CC -3'              150-1

SEQ ID NO. 5:
5' CGC TGG AGC ATA TGT TAT TCC TCC TT 3'               150-2

SEQ ID NO. 6:
5' AGC GTC TGC GTA TTG TAC GTG GTA 3'                  150-3

SEQ ID NO. 7:
5' TGG GTA CCA CGT ACA ATA CGC AGA 3'                  150-4

SEQ ID NO. 8:
5' CCC AGC TCT TCG AAG ATA ACT ACG CAC TGG CTG T 3'    150-5

SEQ ID NO. 9:
5' CAGTAC AGC CAG TGC GTA GTT ATC TTC GAA GAG C 3'     150-6

SEQ ID NO. 10:
5' ACT GGA CAA CGG TGA TCC TCT GAA CAA 3'              150-7

SEQ ID NO. 11:
5' GGT GTT GTT CAG AGG ATC ACC GTT GTC 3'              150-8

SEQ ID NO. 12:
5' CAC CAC TCC GGT AAC TGG TGC TTC TCC 3'              150-9

SEQ ID NO. 13:
5' GCC AGG AGA AGC ACC AGT TAC CGG AGT 3'              150-10
```

TABLE 1-continued

```
SEQ ID NO. 14:
5' TGG CGG TCT GCG TGA ACT GCA GCT CCG T 3'        150-11

SEQ ID NO. 15:
5' AGC TAC GGA GCT GCA GTT CAC GCA GAC C 3'        150-12

SEQ ID NO. 16:
5' AGC TTG ACT GAA ATC CTC AAA GGT G 3'            150-13

SEQ ID NO. 17:
5' ACG CCA CCT TTG AGG ATT TCA GTC A 3'            150-14

SEQ ID NO. 18:
5' GCG TAC TGA TCC AGC GTA ACC CTC A 3'            150-15

SEQ ID NO. 19:
5' CAG CTG AGG GTT ACG CTG GAT CAG T 3'            150-16

SEQ ID NO. 20:
5' GCT GTG CTA TCA GGA TAC TAT CCT 3'              150-17

SEQ ID NO. 21:
5' CCA CAG GAT AGT ATC CTG ATA GCA 3'              150-18

SEQ ID NO. 22:
5' GTG GAA AGA CAT CTT CCA CAA GA 3'               150-19

SEQ ID NO. 23:
5' TTG TTC TTG TGG AAG ATG TCT TT 3'               150-20

SEQ ID NO. 24:
5' ACA ACC AGC TGG CTC TGA C 3'                    150-21

SEQ ID NO. 25:
5' CAG AGT CAG AGC CAG CTG G 3'                    150-22

SEQ ID NO. 26:
5' TCT GAT CGA CAC CAA CCG TTC TCG AGC TTA ATA G 3'   150-23

SEQ ID NO. 27:
5' GAT CCT ATT AAG CTC GAG AAC GGT TGG TGT CGA T 3'   150-24
```

The oligonucleotides were synthesized on an Applied Biosystems 380B DNA synthesizer using phosphoramidite chemistry (Caruthers, Science 230, 281 (1985)). The HER-2/neu synthetic gene fragment was assembled in two sections of 12 oligonucleotides each. The 5' gene section consisted of oligonucleotides 150-1 through 150-12 assembled as shown in FIG. 1A (SEQ ID NO. 1 and SEQ ID NO. 2) and contained XbaI and pseudoHindIII ends. The 3' gene section consisted of oligonucleotides 150-13 through 150-24 assembled as shown in FIG. 1A and contained pseudoHindIII and BamHI ends. The pseudoHindIII to BamHI gene section was cloned into the HindIII and BamHI polylinker sites of pCFM1156 (Burnette et al. Bio/Technology 6, 699–706 (1988)). The 5' gene section was then cloned into the XbaI and HindIII sites to complete assembly of the HER-2/neu gene fragment. This construct, designated pCFM1156/HER-2/neu, allowed the direct expression of the HER-2/neu a gene fragment by induction of the temperature sensitive promoter in pCFM1156. The synthetic gene fragment was confirmed to be as designed by DNA sequencing.

The HER-2/neu (96–191) polypeptide was purified as follows. A 300 ml overnight culture of the pCFM1156/HER-2/neu in E. coli strain FM6 (ATCC accession no. 53910) was grown at 30° C. in LB media containing 50 µg/ml kanamycin. The overnight innoculum was added to a 5 L fermentation vessel containing 5 L standard media (Standard media is per L: 2.3 g KOH; 0.9 g $KH_2PO_4$; 4.5 g $K_2HPO_4$; 14.3 g yeast extract; 29.6 g $(NH_4)_2SO_4$; 11.25 g glucose; 0.92 g $MgSO_4$ and is supplemented with trace metals, vitamins and thiamin). The fermentation was run at 30° C. until the $OD_{600}$=1.5. Temperature was shifted to 42° C. and the fermentation continued until the final $OD_{600}$=11.2. The bacteria were collected by centrifugation and the supernatant was discarded. The cell pellet was resuspended in 150 ml of distilled $H_2O$. Disruption of the cells was performed by passing the cell suspension through a Microfluidizer Model 110Y. The solution was centrifuged to pellet the inclusion bodies which were resuspended in distilled $H_2O$ at a final volume of 50 ml.

A portion (5.0 ml) of the HER-2/neu protein inclusion body suspension was pipetted into a 50 ml conical bottom centrifuge tube. 5.0 ml of 8.0 M guanidine/100 mM dithiothreitol/50 mM Tris-HCl pH 8.0 was added to the suspension. The mixture was sonicated to solubilize the inclusion bodies. The solution was diluted to 0.5 M guanidine with 50 mM Tris-HCl pH 8.0. The precipitate was collected by centrifugation and solubilized in 20 ml of 30% acetonitrile/70% 50 mM Tris-HCl pH 8.0 with sonication. The solution was filtered through a 0.45 µ filter. 14 ml of the filtrate was purified by reverse phase HPLC on a 1.0 cm×30 cm Vydac 3000 Å wide pore C18 column with a mobile phase gradient of 30–45% B/15 min, where A was 0.1% trifluoroacetic acid in water and B was 0.05% trifluoroacetic acid in acetonitrile, at a flow of 3.0 ml/min. Fractions containing HER-2/neu extracellular domain peptide were pooled and lyophilized. The yield of peptide from 14 ml of filtrate was 2 mg. The purified protein was found to have the predicted amino-terminal sequence and amino acid composition.

EXAMPLE 2

Generation of HER2 Monoclonal Antibodies

Antibodies to HER-2/neu extracellular domain were generated using standard techniques such as those described in Harlow and Lane Antibodies: *A Laboratory Manual*, Cold Spring Harbor Laboratory (1988).

2 mg of purified HER-2/neu extracellular domain prepared as described in Example 1 were suspended in 1 ml of 0.1 M phosphate buffer, pH 7.5, and 50 µl of 1 M carbonate/bicarbonate buffer were added to bring the pH to about 9.5. 10 µl aliquots of dimethyl suberimidate (10 mM in $H_2O$) were added at one hour intervals with stirring at room temperature and the mixture was incubated at 37° C. After the third addition of suberimidate, 100 µl (500 µg) of adjuvant peptide (N-acetyl muramyl L-alanyl D-isoglutamine; Sigma Chemical Co., St. Louis, Mo.) were added and the mixture was incubated at 30° C. for an additional two hours. The mixture was then diluted to 2 ml by addition of 820 µl of 0.1 M phosphate buffer, pH 6.0 and 1 ml was emulsified with 1 ml of complete Freund's adjuvant.

Ten mice were each injected with 100 µl of emulsion and eleven days later each received a second injection. About five weeks later, test bleeds of each mouse were taken, serum was recovered and diluted 1:100 with sterile PBS, and binding to HER-2/neu extracellular domain was determined on each serum sample. Each well of Immulon microtiter plates was coated with 100 µl of a 3 µg/ml solution of HER-2/neu extracellular domain polypeptide in 20 mM phosphate buffer, pH 7.5 (300 ng/well) and incubated at 4° C. overnight. 2.5% bovine serum albumin (BSA) was diluted 1 to 1 with distilled water and 200 µl of the resulting solution were added to each well without removal of HER-2/neu protein solution. The plates were then incubated at 37° C. for 1.5 hrs and the contents of the wells removed. 100 µl of 0.25% BSA in PBS were added to each well and 100 µl of ten different mouse antisera were added starting with a 1 to 200 dilution of antiserum and continuing with serial two-fold dilutions to 1 to 25,600. The plates were incubated at room temperature for two hours, then the contents of the well were removed, the wells washed four times with TEN buffer and 100 µl of a 1 to 4000 dilution of goat anti-mouse horseradish peroxidase conjugate (Kirkegaard and Perry Laboratories) was added to each well. The secondary antibody conjugate was incubated for about two hours at room temperature, the contents of the wells were removed and the wells were washed four times with TEN buffer. 100 µl of 0.1 M phosphate buffer and 50 µl of a solution of 3',3',5',5' tetramethylbenzidine and hydrogen peroxide were added to each well and incubated at room temperature for one hour. 50 µl of 0.5 N $H_2SO_4$ were then added to each well and samples analyzed on a plate reader against an air blank. The top five responding mice were designated in order A9, A3, A10, A1 and A2.

Spleens from the top five responding mice were removed, the cells dispersed and fused with SP2/0 mouse myeloma cells (ATCC accession no. CRL1581). The fusions were cultured in microtiter plates in HAT selection medium using standard techniques. Cell culture supernatants were titered for antibodies reacting with the HER-2/neu extracellular domain using the procedures described above for serum samples. Hybridomas designated 9C2, 11G5 and 5A11 were determined to have the highest titers. They were subjected to dilution cloning and second dilution clone hybridoma supernatants were screened for antibodies reacting with the HER-2/neu extracellular domain. A number of strongly positive clones were observed. The following clones were selected for injection into mice for production of ascites fluid: 9C2C1A9, 9C2B10F12, 11G5B3H7 and 11G5G1B11.

Isotypes of 9C2 and 11G5 monclonal antibodies were determined using standard procedures described in Harlow and Lane, supra. The isotype of 9C2 was $IgG_1$ and the isotype of 11G5 was an $IgG_1/IgG_{2b}$ chimera.

EXAMPLE 3

A. Immunocytochemical staining of cells expressing high levels of the HER-2/neu protein Cultured cell lines were fixed with Saccomanno fluid and immunoperoxidase stained with either 9C2 antibody, 11G5 antibody, positive control 9G6 antibody (known to recognize $p185^{HER-2/neu}$), or irrelevant negative control MOPC21 antibody. The SK-BR-3 human breast adenocarcinoma cell line (ATCC accession no. HTB 30) was obtained from the American Type Culture Collection (Rockville, Md.) and cultured in RPMI 1640 medium supplemented with 10% fetal bovine serum (heat-inactivated) and 1×L-glutamine. CHO-HER-2 B7 cells, which are Chinese hamster ovary (CHO) cells transfected with a vector that directs expression of elevated levels of human $p185^{HER-2/neu}$ protein, and CHO-PCN cells, which are transfected with a negative control vector, were prepared generally as described in Slamon et al. Cancer Cells 7, 377–384 (1989). The growth medium for CHO-HER-2 B7 and CHO-PCN cells was α-minimum essential medium without nucleotides containing 50 nM methotrexate, 0.75 mg/ml G418 and 10% dialyzed fetal bovine serum. Cells were cultured in Leighton tubes (Costar) which contain plastic inserts. These inserts can be removed with cells attached for staining and microscopic examination. Approximately $5-10 \times 10^4$ cells were seeded per Leighton tube. The cells were cultured for three days to 60–80% confluency. The Leighton tube inserts with attached cells were removed, rinsed in phosphate-buffered saline (PBS; 10 mM sodium phosphate, pH 7.5, 150 mM NaCl), immersed for 20 min in Saccomanno Fluid (Lerner Laboratories, Pittsburgh, Pa.), allowed to dry at room temperature, and stored at room temperature. The cells were rehydrated prior to immunoperoxidase staining by immersing the Leighton tube inserts in 95% ethanol for 10 min, and then in PBS for 10 min. Immunoperoxidase staining used Elite ABC kits according to the manufacturer's directions (Vector Laboratories, Inc., Burlingame, Calif.). The rehydrated cells were first covered with 1.5% normal horse blocking serum. The blocking serum was removed after 20 min and replaced with either irrelevant negative control mouse IgG1 antibody MOPC21 (2 µg/ml; Sigma Chemical Co., St. Louis, Mo.), anti-$p185^{HER-2/neu}$ positive control antibody 9G6 (5 µg/ml; Oncogene Science, Inc., Uniondale, N.Y.), protein G-purified antibody 9C2 (2 µg/ml), or protein G-purified antibody 11G5 (2 µg/ml). Protein G purification of antibodies (dilution clones 9C2C1A9 and 11G5G1B11) from ascites fluid was carried out on GammaBindG™ Agarose (Genex, Gaithersburg, Md.) following procedures recommended by the manufacturer. After 60 min incubation with one of these four antibodies, the Leighton tube inserts with attached cells were rinsed with PBS and then immersed in PBS for 10 min. Antibody localization was detected with a 30-min incubation with biotinylated anti-mouse IgG antibody, a 10-min immersion in PBS, a 30 min incubation with preformed avidin:biotinylated horseradish peroxidase complexes (Vectastain Elite ABC reagent), another 10-min immersion in PBS, and a 6-min development with 3,3'-diaminobenzidine/$H_2O_2$ substrate. The attached cells were then immersed in H$_2$O for 10 min, dehydrated by two 3-min immersions in 95% ethanol, two 3-min immersions in 100% ethanol, and 25 dips in xylene. The Leighton tube inserts were attached to glass microscope slides and coverslipped with Permount (Fisher). Brown staining, revealing sites of antibody binding, was observed on individual cells using light microscopy.

Figure 2B:
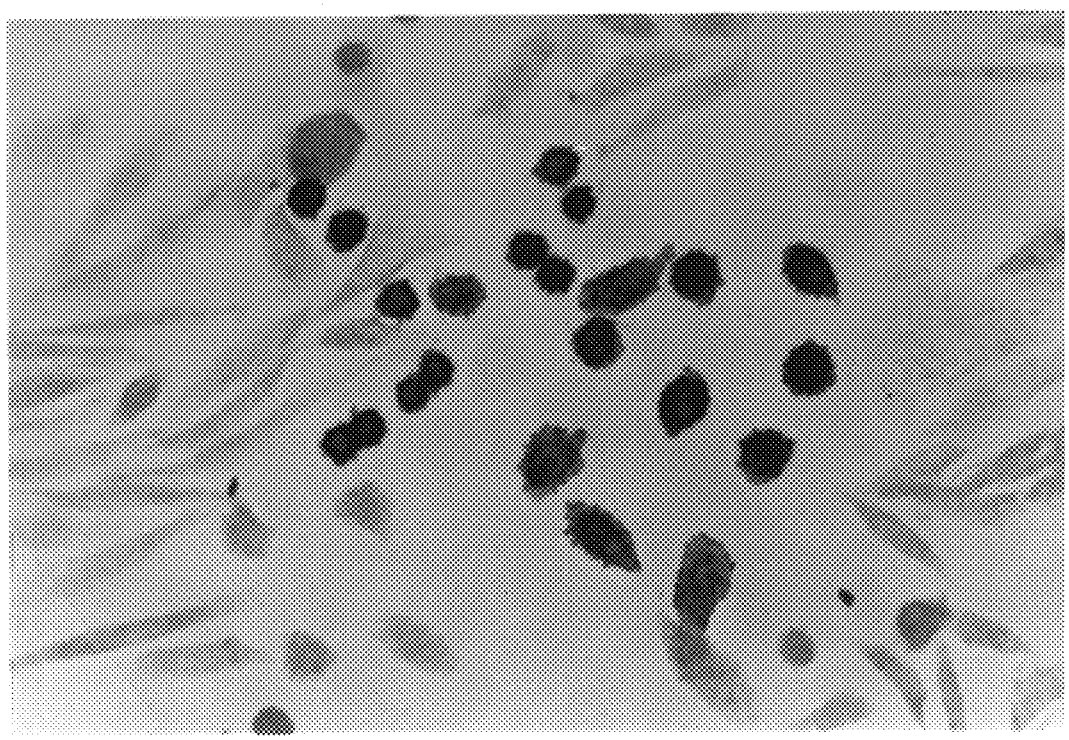
Figure 2C:
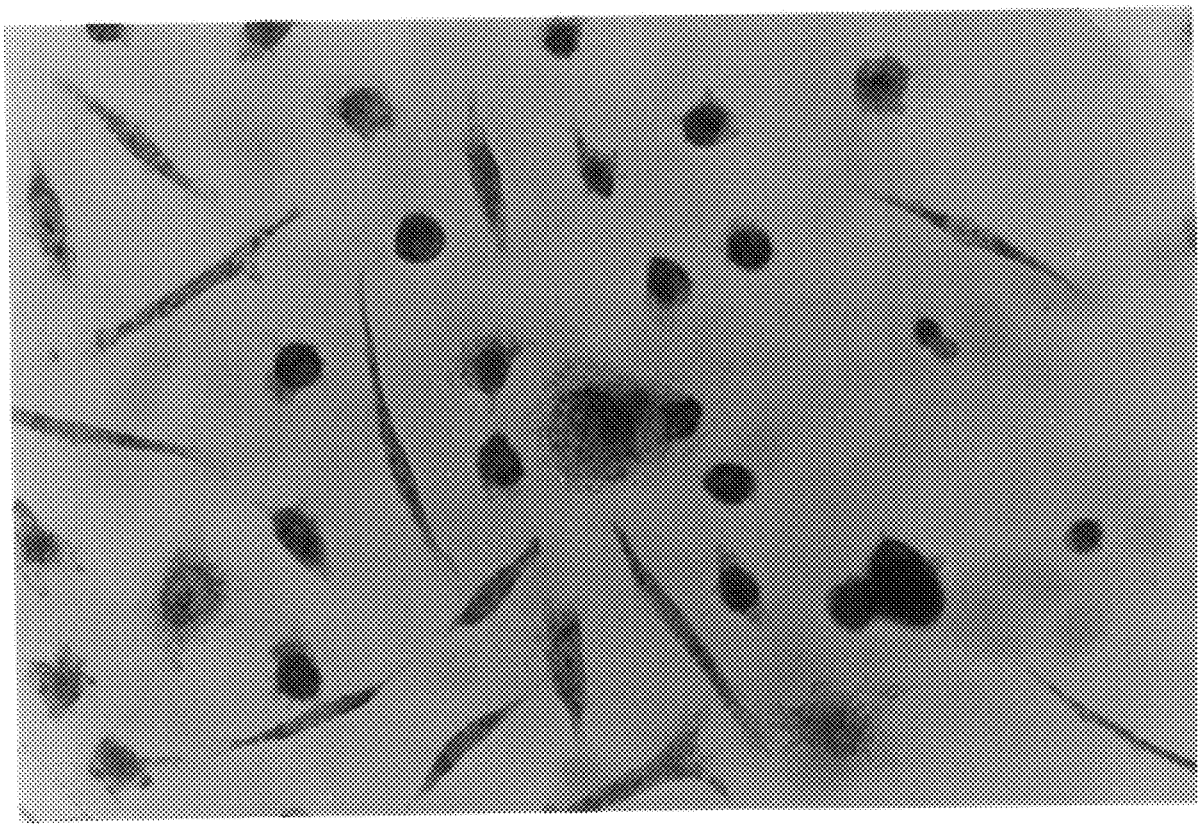
Figure 3A:
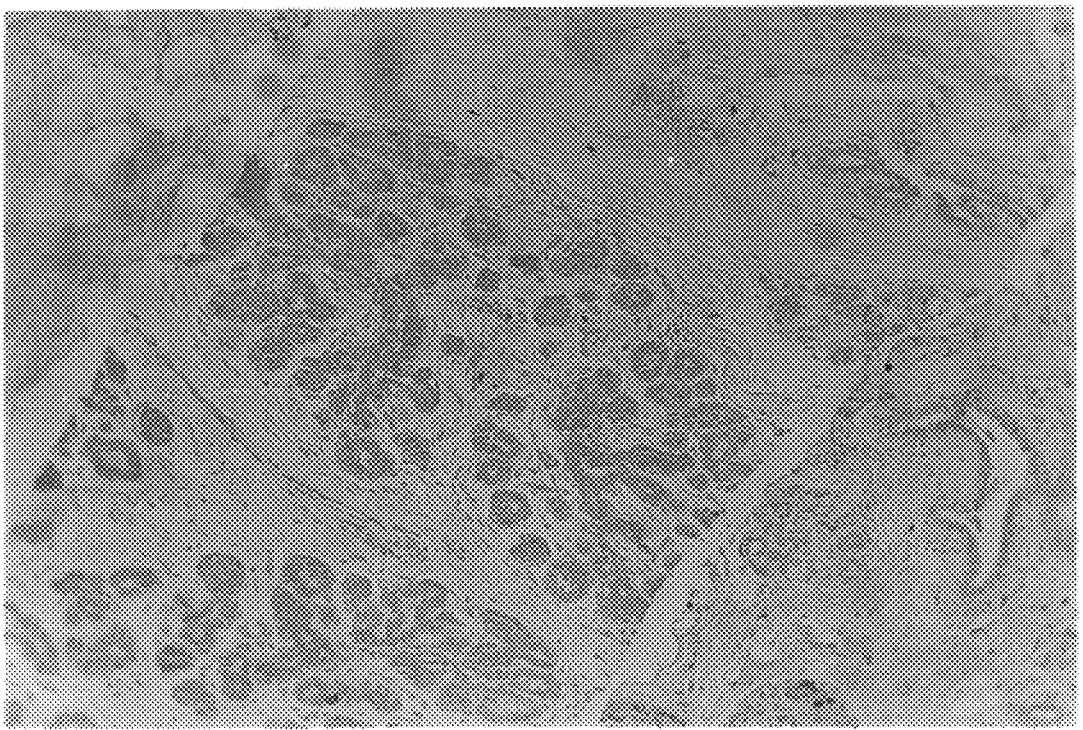
FIG. 3. Immunohistochemical staining of paraffin-embedded, formalin-fixed human breast tissue specimens. Breast specimens in multitissue slides were immunohistochemically stained with either antibody 11G5 (panels a and b) or antibody 9C2 (panels c and d). Panels a and c show staining of normal breast specimens. Panels b and d show staining of breast tumor specimens. All prints represent identical exposure times.
Figure 3B:
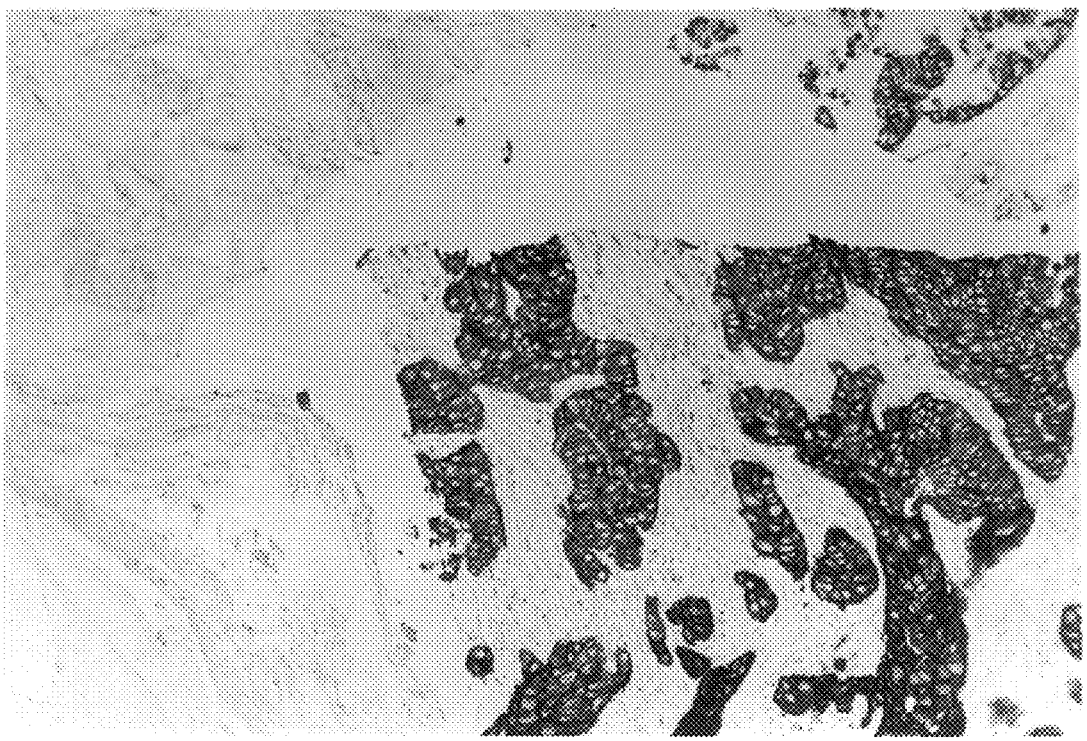
Figure 3C:
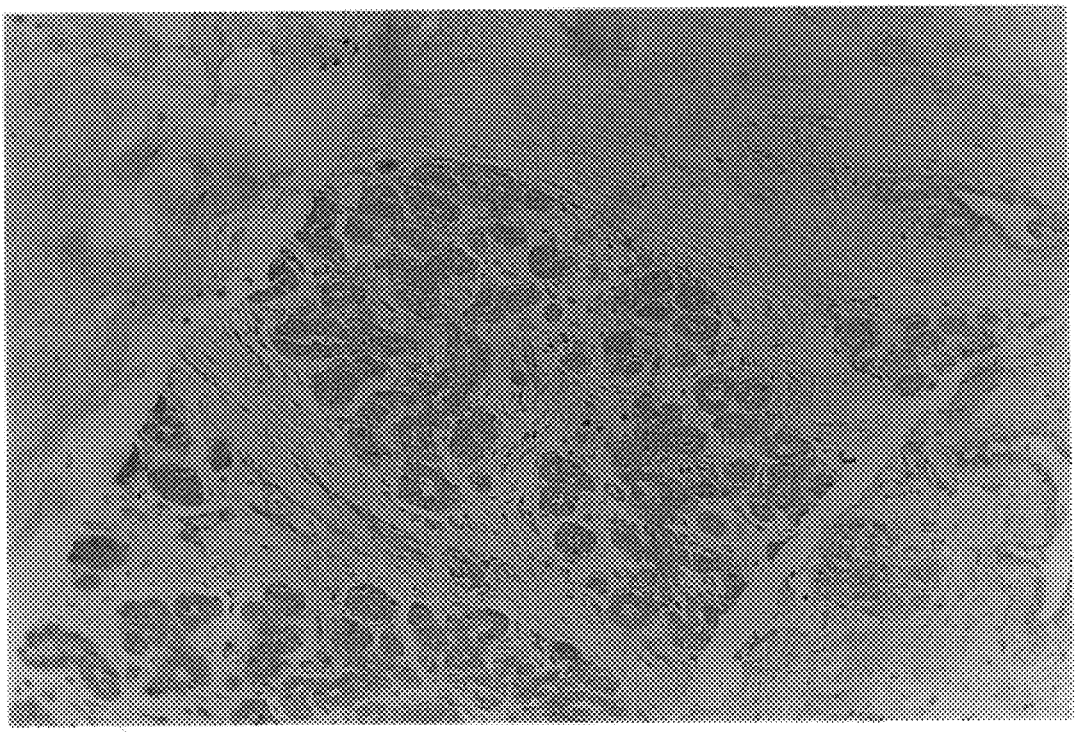
Figure 3D:
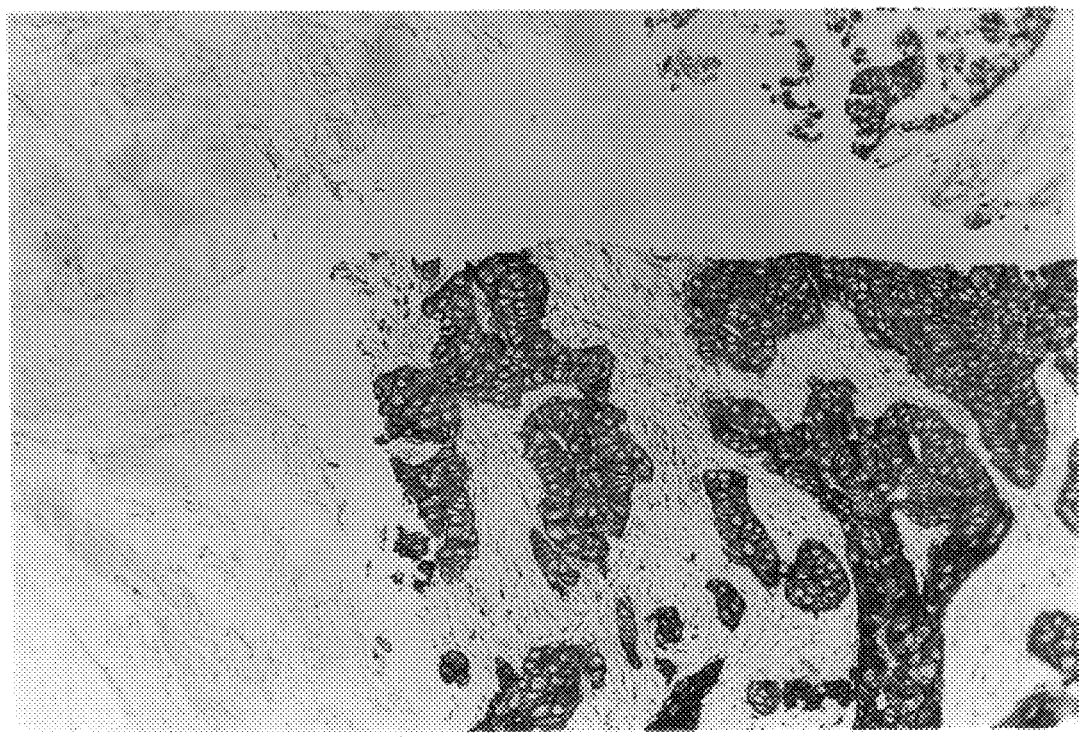

Antibody 9C2 staining gave intense brown positive staining of SK-BR-3 breast carcinoma cells (FIG. 2, panel a), which express high levels of p185$^{HER-2/neu}$ protein (Scott et al., J. Biol. Chem. 266, 14300–14305 (1991)). In the CHO/HER-2 cultures, the 9C2 antibody identified clusters of positively staining cells in a field of unstained cells (FIG. 2, panel b), and gave weak background staining of the CHO-PCN cells (FIG. 2, panel c). Antibody 11G5 gave similar staining patterns. The anti-p185$^{HER-2/neu}$ positive control antibody 9G6 also provided similar staining patterns, while the negative control MOPC21 antibody yielded only weak background staining. These experiments show that antibodies 9C2 and 11G5 selectively stain cells expressing elevated levels of p185$^{HER-2/neu}$ protein. Furthermore, the selective staining with 9C2 and 11G5 antibodies was obtained after processing the cells with a clinical cytology fixation procedure (Saccomanno, Lab. Med. 10, 523–527, 1979).

B. Immunohistochemical staining of human tissue sections

Breast multitissue sections were stained with either 9C2 antibody, 11B5 antibody, positive control pAb1 antibody (Triton Biosciences, Inc., Alameda, Calif.), or irrelevant negative control MOPC141 antibody. Multitissue breast tissue slides (catalog number 88 BTF-4), prepared according to the method of Battifora (Lab. Invest. 55, 244–248 1986), were purchased from Xenetics Biomedical, Inc., (Irvine, Calif.). Each microscope slide had a section of a paraffin block containing multiple formalin-fixed human breast specimens. Normal breast specimens, benign fibroadenoma breast specimens, and breast tumor specimens were organized into different compartments. Paraffin was removed from the sections by heating at 60° C. for 30 min and immersion in xylene for 6 min. The tissue specimens were rehydrated by immersing the slides for 6 min in 100% ethanol, then 6 min in 95% ethanol, and finally 10 min in PBS. Immunoperoxidase staining used Elite ABC kits according to the manufacturer's directions (Vector Laboratories,.Inc., Burlingame, Calif.). The specimens were covered with 1.5% normal blocking serum. The blocking serum was removed after 20 min and replaced with either irrelevant negative control mouse IgG2b antibody MOPC141 (2 µg/ml; Sigma Chemical Co.), anti-p185$^{HER-2/neu}$ positive control antibody pAb1 (1:30 dilution; Triton Biosciences, Inc.), antibody 9C2 (1:1,000 dilution of ascites fluid), or antibody 11G5 (1:1,000 dilution of ascites fluid). After 60 min incubation with one of these four antibodies, the specimens were rinsed with PBS and immersed in PBS for 10 min. Antibody localization was detected with a 30-min incubation with biotinylated anti-mouse IgG or anti-rabbit IgG antibody, a 10-min immersion in PBS, a 30 min incubation with preformed avidin:biotinylated horseradish peroxidase complexes (Vectastain Elite ABC reagent), another 10-min immersion in PBS, and a 6-min development with 3,3'-diaminobenzidine/H$_2$O$_2$ substrate. The specimens were then placed in H$_2$O for 10 min, and counterstained by immersion for 10 min in 0.1 M sodium acetate, pH 4, prior to a 10-min staining in ethyl green (Cell Analysis Systems, Inc., Elmhurst, Ill). Following counterstaining, the sections were quickly rinsed several times in H$_2$O and in 1-butanol, cleared in xylene, and coverslipped with Permount (Fisher).

Immunohistochemical staining of breast multitissue slides with anti-p185$^{HER-2/neu}$ antibody 9C2 and 11G5 gave positive staining of a subset of the breast tumor specimens. FIG. 3, panel b shows three adjacent tumor specimens, with two specimens showing strong positive brown staining after immunohistochemical staining with antibody 11G5. Tumor cells in these specimens show heavy membrane staining with some cytoplasmic staining, while stromal cells in the tumor specimens were unstained. This is the expected staining pattern for tumors expressing high levels of p185$^{HER-2/neu}$ (Press, et al., Oncogene 5, 953–962). Antibody 9C2 gave a nearly identical staining pattern (FIG. 3, panel d). These specimens did not stain with the negative control antibody MOPC141. The 11G5 and 9C2 antibodies both gave only weak background staining of normal breast tissue specimens (FIG. 3, panels a and c) and benign breast fibroadenoma specimens. The 11G5 and 9C2 staining patterns were concordant with the staining pattern obtained with positive control anti-p185$^{HER-2/neu}$ antibody pAb1, indicating that the 11G5 and 9C2 antibodies selectively stain tumor cells with elevated levels of p185$^{HER-2/neu}$ in formalin-fixed -and paraffin-embedded human breast tissues.

EXAMPLE 4

Selectivity and Sensitivity of 9C2 and 11G5 Immunostaining of Breast Carcinoma Tissue Samples: A Comparative Study As indicated previously, HER-2/neu overexpression in human breast cancer has been correlated with poor survival in some studies but not in others. In an attempt to resolve this discrepancy, Press and colleagues (Press et al., supra) compared a set of HER-2/neu antibodies for sensitivity and selectivity of immunostaining of breast carcinoma tissues in multi-tissue tumor blocks. The tissue samples used had known levels of HER-2/neu expression as determined by Southern, Northern and Western analysis (Slamon et al. Science (1987), supra; Slamon et al. Cancer Cells (1989), supra). The result of this comparative study are presented in Table 2 of Press et al., supra . In comparison to 27 other anti-p185$^{HER-2/neu}$ antibodies tested, antibody 9C2 was found to have the highest sensitivity in identifying breast cancer samples having HER-2/neu overexpression. At the same time, antibody 9C2 retained 100% specificity. 11G5 showed the second highest sensitivity (along with polyclonal antibody R60) of any of the antibodies tested although the specificity of 11G5 was 92%. It should also be noted that of the top five antibodies shown in Table 2 of Press et al., 9C2 and 11G5 are the only monoclonal antibodies while the other preparations are polyclonal antibodies. This study demonstrates distinct advantages of anti-p185$^{HER-2/neu}$ antibodies 9C2 and 11G5 in the detection of HER-2/neu levels in breast carcinoma tissue samples.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A monoclonal antibody, or fragment thereof, which binds to a denatured epitope comprising a subset of amino acid residues 96–191 of the HER-2/neu protein as shown in FIG. 1B (SEQ ID NO:3), wherein the antibody detects HER-2/neu protein overexpression in cells or tissues with 80% or greater sensitivity.

2. The antibody of claim 1 having a detectable label.

3. The antibody of claim 2 wherein the label is radioactive, chemical, fluorescent or enzymatic.

4. The antibody of claim 1 which is a recombinant antibody.

5. Hybridoma cell lines producing the monoclonal antibody of claim 1.

6. The antibody of claim 1 wherein the cells or tissues are from human tumors.

7. The antibody of claim 6 wherein the cells or tissues are from stomach, breast, lung, pancreatic, prostate or ovarian tumors.

8. A kit for use in detecting HER-2/neu expression in a biological sample comprising an antibody of claim 1 and reagents for detecting HER-2/neu expression.

9. The kit of claim 8 wherein the reagents permit detection of HER-2/neu expression by immunocytochemical or immunohistochemical staining.

10. In a method for detecting HER-2/neu expression in a biological sample wherein the method comprises contacting the sample with an anti-p185$^{HER-2/neu}$ antibody under conditions appropriate for antibody binding to the sample and determining the extent of binding of the antibody to the sample; the improvement comprising contacting the sample with the antibody of claim 1.

11. The method of claim 10 wherein the sample is fluid, intact cell, cell extract or tissue.

12. The method of claim 11 wherein the sample has been treated with a fixative.

13. The method of claim 12 wherein the fixative is an organic solvent or a cross-linking reagent.

14. The method of claim 11 wherein the sample is derived from stomach, breast, lung, pancreatic prostate or ovarian cancer tissue.

15. The method of claim 11 wherein the cell or tissue is from a human tumor.

16. The method of claim 11 wherein the cell or tissue is from a human stomach, breast, lung, pancreatic, prostate or ovarian tumor.

17. The method of claim 10 wherein the extent of binding of antibody is determined by immunocytochemical or immunohistochemical staining.

18. A hybridoma cell line having ATCC accession no. HB11861.

19. A hybridoma cell line having ATCC accession no. HB11862.

* * * * *

UNITED STATES PATENT AND TRADEMARK OFFICE
CERTIFICATE OF CORRECTION

PATENT NO.    : 6,441,143 B1
DATED         : August 27, 2002
INVENTOR(S)   : Raymond A. Koski It is certified that error appears in the above-identified patent and that said Letters Patent is hereby corrected as shown below:

<u>Column 25,</u>
Line 53, replace "cells or tissues" with -- a cancer cell or tissue --.

Signed and Sealed this

Eighteenth Day of February, 2003

JAMES E. ROGAN
*Director of the United States Patent and Trademark Office*